United States Patent
Shimizu et al.

(10) Patent No.: US 7,395,725 B2
(45) Date of Patent: Jul. 8, 2008

(54) SAMPLE TREATMENT APPARATUS AND SAMPLE MEASUREMENT APPARATUS PROVIDING IT

(75) Inventors: Naohito Shimizu, Kyoto (JP); Masahiko Endo, Kyoto (JP); Minoru Ikawa, Kyoto (JP); Poliang Chien, Rancho Palos Verdes, CA (US); James E. Downey, Dana Point, CA (US)

(73) Assignees: Horiba, Ltd., Kyoto (JP); Horiba Instruments Incorporated, Irvine, CA (US)

( * ) Notice: Subject to any disclaimer, the term of this patent is extended or adjusted under 35 U.S.C. 154(b) by 295 days.

(21) Appl. No.: 11/311,066

(22) Filed: Dec. 19, 2005

(65) Prior Publication Data

US 2007/0137316 A1    Jun. 21, 2007

(51) Int. Cl.
*G01N 1/22* (2006.01)
(52) U.S. Cl. .................................. 73/863.12
(58) Field of Classification Search ............... 73/863.83
See application file for complete search history.

(56) References Cited

U.S. PATENT DOCUMENTS 2,814,952 A * 12/1957 Ryant, Jr. et al. ............ 136/200
3,748,906 A * 7/1973 Manka ..................... 73/863.01
4,485,684 A * 12/1984 Weber et al. .............. 73/863.12
4,497,214 A   2/1985 Ramelot
4,779,466 A * 10/1988 Ramsner et al. .......... 73/863.33
5,473,951 A * 12/1995 Tomlin .................... 73/863.83
5,627,328 A * 5/1997 Sheridan et al. .......... 73/863.83
5,753,830 A * 5/1998 Sundh ..................... 73/863.83
6,200,819 B1 * 3/2001 Harvey et al. ............... 436/179

FOREIGN PATENT DOCUMENTS

| EP | 0 208 438 | 1/1987 |
| EP | 0 095 802 | 9/1987 |
| EP | 0 243 569 | 11/1987 |
| JP | 8-224438  | 9/1996 |

* cited by examiner

*Primary Examiner*—Robert R Raevis (57) ABSTRACT

There is provided a sample treatment apparatus which can, continuously and stably for a long time, treat a sample containing an easily precipitating substance such as sulfur and a measuring apparatus providing it. The sample treatment apparatus includes: a path for introducing a fluid for an aspirator, at least two sample flow paths A connected in one side to the path for introducing a fluid for an aspirator and connected in the other side to a sample collecting part, a sample flow path B connected in one side to one sample flow path A passing a fluid for an aspirator and connected in the other side to the other sample flow path A, a cooling part for cooling a part of the sample flow paths A, and a controller for selecting and switching the sample flow paths A into which a fluid for an aspirator is introduced.

20 Claims, 6 Drawing Sheets

SAMPLE TREATMENT APPARATUS AND SAMPLE MEASUREMENT APPARATUS PROVIDING IT

BACKGROUND OF THE INVENTION

1. Field of the Invention

The present invention relates to a sample treatment apparatus for treating coexistent components adhering to a sample flow channel and a measuring apparatus for providing it.

2. Description of the Related Art

In a process of producing various petroleum products from heavy oil as raw material, a gas containing a large amount of hydrogen sulfide ($H_2S$) discharged from a refining apparatus, a catalytic cracking apparatus or the like, generates sulfur dioxide ($SO_2$) significantly when the discharged gas is used directly as fuel gas, so conventionally the gas is used after sulfur contained therein is removed by a sulfur recovery apparatus. Specifically, the recovery of sulfur comprises a step of separating $H_2S$ from the gas and a step of converting the separated $H_2S$ into element sulfur (Sv). The former step uses a method that involves absorbing $H_2S$ into an aqueous alkaline solution of monoethanolamine etc. and then separating and recovering it, and the latter step widely uses the Claus process or Super Claus process.

As the most important and effective sulfur recovery process, the Claus process or Super Claus process is used in gas treatment, in natural gas and cokes plants and in a refining apparatus. In this process, a part of the acidic gas stream is oxidized to generate $SO_2$. Thereafter, $SO_2$ reacts with remaining $H_2S$ to form sulfur in the presence of a catalyst. Due to easiness and efficiency, the Claus process is useful in recovery of sulfur and utilized more often worldwide than in any other plants.

The Claus process is a process wherein $H_2S$ is converted into Sv by the following chemical reactions:

(1) $H_2S$ is partially combusted with air in a reaction furnace and partially formed into $SO_2$.

$$3H_2S+3/2O_2=2H_2S+SO_2+H_2O \quad (1)$$

(2) Then, this gas is introduced into a catalytic reaction tower (catalytic reaction means) to form gaseous Sv.

$$2H_2S+SO_2=3Sv+2H_2O \quad (2)$$

By the Claus process shown above, the recovery of sulfur is sometimes known to be as high as 98% or more.

Throughout the stoichiometric reactions in the catalytic reaction tower, the critical ratio in the Claus process should be kept at 2:1 to obtain Sv surely in a good yield. This is evidence from the fact that when the ratio is 2:1 or more, excessive oxygen ($O_2$) is necessary in the process. Because air is used in combustion in the reaction furnace, the oxygen demand in the reaction shall usually be the air demanded for the reaction.

Figure 5:
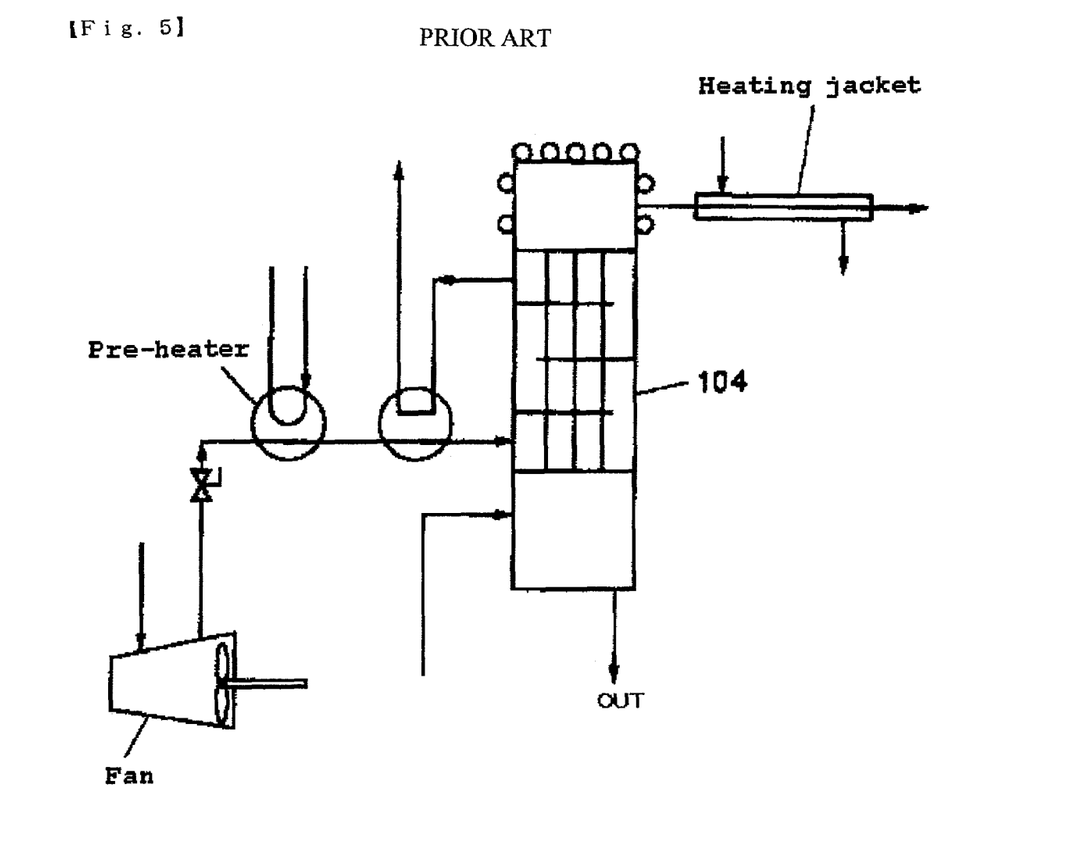
FIG. 5 is an explanatory drawing illustrating a method of recovering sulfur in the Claus process in the prior art.
Figure 6:
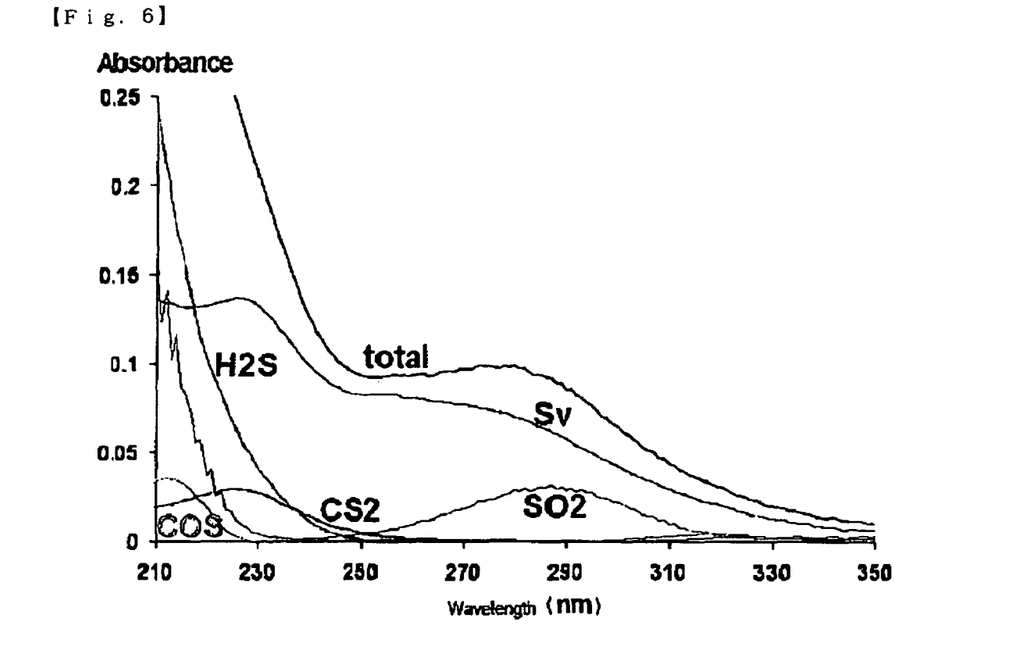
FIG. 6 is an explanatory drawing schematically showing ultraviolet absorption characteristics of the compounds in the Claus process.
Figure 7:
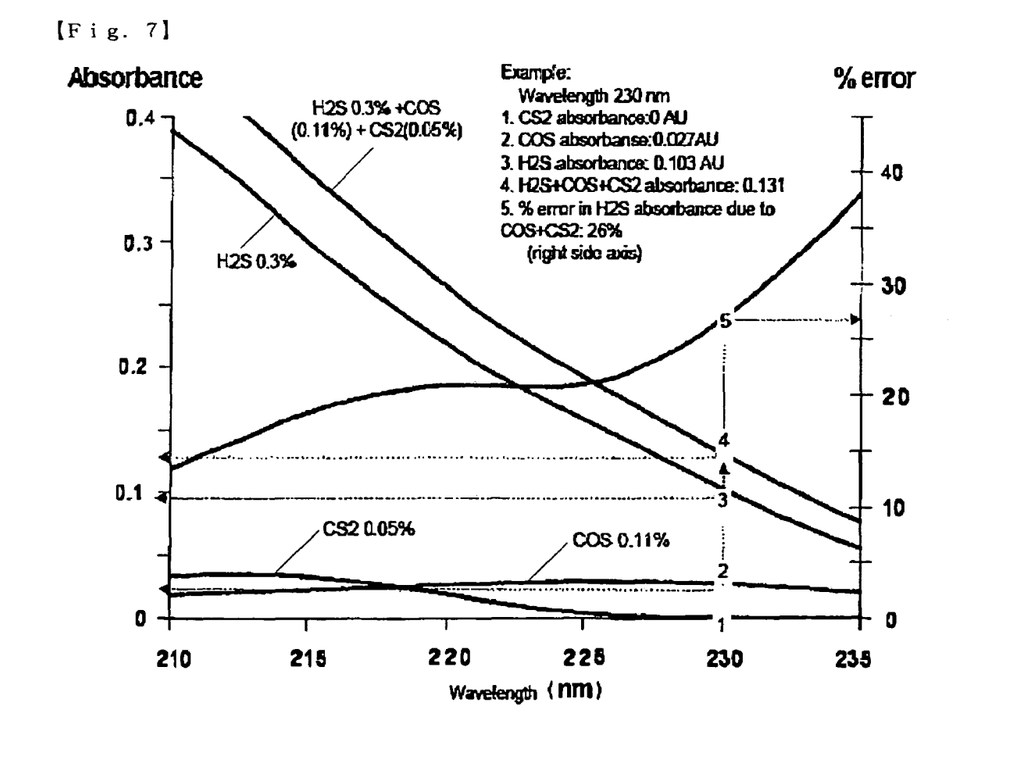
FIG. 7 is an explanatory drawing schematically showing interference influence in measurement of $H_2S$.

As the method of removing and recovering Sv from the gas stream in the Claus process described above, there is proposed a method that involves cooling the gas to be processed, whereby Sv in the form of steam and/or entraining particles is removed from the gas. Specifically as shown in FIG. 5, the gas to be processed is led toward the lower end of a heat exchanger 104, and it is guaranteed by the temperature and/or the flow rate of a refrigerant that the temperature of a wall surface of the heat exchanger 104 is not higher than the solidification point of sulfur, or is not lower than the dew point of water if any in the gas. By the action of gravity, the precipitated Sv is removed toward the direction opposite to the flow of the gas to be processed (see, for example, JP-A 8-224438).

In the Claus plant or the like, however, the recovery of sulfur is influenced significantly by the concentration of $H_2S$ and $SO_2$ involved in the reaction, and thus it is important to measure the concentration of $H_2S$ and $SO_2$. That is, accurate measurement of $H_2S$ and $SO_2$ is key to optimization of the sulfur recovery process. Examples of the measurement method include a method of using ultraviolet (UV) absorption spectrometry capable of separate and direct measurement of $H_2S$ and $SO_2$ or a method that involves oxidizing a reducing sulfur compound such as $H_2S$ into $SO_2$ to measure the concentration of $H_2S$ indirectly by infrared (IR) absorption spectrometry thereby determining the concentration of $H_2S$ and $SO_2$.

Because of Sv and water present in the process gas, the measurement may undergo the interference influence attributable to overlapping of absorption spectra of $H_2S$ and $SO_2$ or influence attributable to splashing, clogging resulting or the like from aggregation. Particularly in measurement of a sample collected in a process and in measurement by a directly inserted measuring apparatus, the operation of the measuring apparatus in a suitable state for 4 to 8 months is necessary, and thus such influence cannot be neglected.

In the former measuring apparatus of sample collection type, an apparatus for removing Sv is necessary in an absorbance measuring unit in measuring $H_2S$ and $SO_2$, in order to eliminate the interference influence caused for example by highly UV absorption characteristics of Sv. Further, crystallization and clogging with Sv occur easily, thus making it necessary to remove easily solidified substances such as Sv in a sample treating part in the measuring apparatus of sample collection type.

In the directly inserted measuring apparatus, a cold trapping system is used sometimes to eliminate the contamination of a measuring flow cell with sulfur, but crystallized sulfur is layered to form a thermally insulating layer, resulting in failure to maintain a suitable cooling function. Elimination of such excessive sulfur is problematic.

It is generally difficult to continuously measure a gas containing not only the above-mentioned Sv but also a gas containing crystallizing or condensing/solidifying substances (for example, tar in coal liquefied gas), and at present, a gas is collected in, for example, a Tedrer® bag and analyzed batchwise.

When a means (e.g. a feed pump) of exerting an influence on the pressure or temperature of a sample is arranged in a sample collection system to measure such a gas, the change in the pressure or temperature may induce generation of condensates thereby.

SUMMARY OF THE INVENTION

To cope with such demand, the object of the present invention is to provide a sample treatment apparatus which can, continuously and stably for a long time, treat a sample containing an easily precipitating substance such as sulfur and a measuring apparatus providing it, which can measure a sample highly accurately, stably for a long time and continuously.

The sample treatment apparatus of the present invention comprises a path for introducing a fluid for an aspirator, at least two sample flow paths A connected in one side to the path for introducing a fluid for an aspirator and connected in the other side to a sample collecting part, a sample flow path B connected in one side to one sample flow path A passing a fluid for an aspirator and connected in the other side to the other sample flow path A, a cooling part for cooling a part of the sample flow paths A, and a controller for selecting and switching the sample flow paths A into which a fluid for an aspirator is introduced, wherein a fluid for an aspirator is introduced into at least one sample flow path A thereby cleaning the sample flow path A and simultaneously suctioning the sample from at least one sample collecting part connected to the other sample flow path A, cooling the sample in the sample flow path A, condensing and removing a specific component in the sample, and introducing the sample into the sample flow path B, and simultaneously selecting and switching, in a predetermined cycle, the sample flow path A into which a fluid for an aspirator is introduced.

For example, an apparatus for measuring the concentration of $H_2S$ and $SO_2$ in monitoring the recovery of sulfur fulfills an important roll in the Claus plant. For continuous and highly accurate measurement of a sample containing an easily precipitating substance, it is important how such substance is efficiently eliminated without introduction into a measurement system such as a sample cell, and simultaneously it is important how precipitation of such substance is prevented by suppressing a change in a sample retaining area and in sample states such as pressure in collecting a sample.

In the present invention, a cooled flow path is arranged in the sample treating part to allow precipitates to adhere to an internal surface of the flow path, thereby removing components exerting interferential influence and causing clogging. By using an aspirator as a means of introducing a sample, a driving unit requiring maintenance is unnecessary, and a site where precipitates can occur in the sample flow path is minimized and continuous use for a long time is feasible, and use of a fluid for an aspirator in cleaning the precipitates is effective in eliminating necessity for separately preparing a fluid for cleaning. Further, a combination of at least two sample flow paths is arranged, and sampling in one flow path, precipitation in the flow path, and cleaning of the precipitates in the other flow path are sequentially repeatedly carried out, whereby a sample treatment apparatus capable of treating a sample highly continuously and stably for a long time can be provided. By precipitating and removing components influencing measurement accuracy, measurement accuracy that cannot be achieved by the conventional method can be secured.

The present invention relates to the sample treatment apparatus wherein the fluid for an aspirator is steam.

As described above, one aspect of the present invention is characterized in that the aspirator functions not only as a suctioning means of introducing a sample but also as a means of cleaning adhering substances. Accordingly, a fluid having a significant cleaning effect and increasing suction performance is used preferably in the aspirator. In the present invention, precipitates such as Sv condensing upon cooling are removed, and by using steam as the fluid for an aspirator, adhering materials are heated and dissolved, and a strong cleaning effect with a high-speed fluid can be utilized.

The present invention relates to the sample treatment apparatus wherein the sample is a process fluid of the Claus process, and at least the sample collecting part is inserted directly into a process line.

In the Claus process, the sample itself contains a large amount of easily crystallizing and easily adhering substances, and it is thus difficult to transfer the sample from a sample collection site to a measurement site. Accordingly, the treatment such as cooling is conducted preferably in the nearest position to the process line. In the present invention, the sample collecting part is inserted directly into the process and immediately treated, thereby coping with such demand, and the measuring apparatus is constituted by combination with measurement functions described later, whereby a measuring apparatus capable of measuring a sample highly continuously and stably for a long time can be provided. By discharging a large amount of the fluid for an aspirator used in cleaning the sample flow path A into the process, a separate apparatus for treating exhaust gas is not necessary.

The present invention provides a measuring apparatus provided with the sample treatment apparatus, wherein the sample flow path B is connected to a sample cell part.

In the present invention, the sample treatment apparatus itself has sample treatment functions, and thus the measuring apparatus is preferably an apparatus directly measuring a processed sample as the subject. Specifically, the measuring apparatus is preferably the utilizing light (e.g. ultraviolet or infrared light) absorption characteristics, and particularly a sample from which precipitates are removed by the sample treatment apparatus is introduced into the sample cell part kept at a predetermined temperature and simultaneously measured, whereby the measuring apparatus integrated with the sample treatment apparatus can be constituted. By connecting the other sides of at least two sample flow paths B to the sample cell part and switching the sample alternately or successively, whereby an almost continuously cleaned sample can be measured. Accordingly, a measuring apparatus capable of continuously measuring a sample highly accurately and stably for a long time can be provided.

The present invention provides the measuring apparatus provided with a heating part including the sample flow path B and the sample cell part, wherein the heating part can be controlled at temperature higher than in the cooling part.

For removing easily precipitating substances contained in a sample in the Claus plant or the like, cooling treatment in the sample flow path A is effective as described above. On the other hand, the sample cell part is preferably controlled at approximately constant temperature for stabilizing e.g. light absorption characteristics, and this also applies to the flow path for connecting it. In the present invention, the heating part and cooling part are separately arranged, and the temperature of the heating part is controlled at temperature higher than in the cooling part, whereby the temperature of each part can be controlled so as to correspond to the function of each part.

The present invention relates to the measuring apparatus wherein the heating part is divided into a first disk containing a flow path for introducing a heating fluid, a check gas, a calibration gas or a cleaning gas, a second disk for accommodating the sample cell part, and a third disk having a path for introducing a fluid for an aspirator, and is composed of the respective disks connected to one another.

The measuring apparatus of the present invention is composed of a sample treatment system, a detection system and a detection auxiliary system for calibration gas, and the respective systems are different from one another in functions and also in regulating temperature. In the present invention, the respective systems are composed of the three divided disks in the heating part, whereby regulation adapted to independent functions or feed of a sample etc. can be achieved.

The present invention relates to the measuring apparatus wherein an optical fiber is connected to the sample cell part to detect absorbance, thereby measuring the concentration of a specific component in a sample.

As described above, a measuring apparatus that can be inserted directly into the process is useful in measurement of a sample in the process. In a measuring apparatus utilizing absorption spectrometry, there are cases where an element constituting the optical system is hardly durable to high temperatures in the process, or temperature regulation is not feasible. In the present invention, therefore, an optical fiber is connected to the sample cell part in the measuring apparatus to detect absorbance to measure the concentration of a specific component in a sample, thereby having heat resistance property and eliminating conditions such as dust adversely influencing the optical system, whereby a measuring apparatus capable of continuously measuring a sample highly accurately and stably for a long time can be provided.

The present invention relates to the measuring apparatus, wherein the background in the measurement system can be calibrated by linking with the switching cycle in the step described above.

The measuring apparatus is constituted such that at least 2 aspirator-connecting flow paths are connected to the sample cell part. Accordingly, a fluid for an aspirator can be introduced into the sample cell part for a short time upon switching the flow path. That is, the fluid for an aspirator is based on a cleaning fluid such as steam, so the fluid for an aspirator can be introduced into the sample cell part to clean the sample cell part. Because the output of the measuring apparatus in this time corresponds to a measured value of background in the absence of measurement component, the background of the measurement system can be calibrated on the basis of this output. That is, in measurement of a sample containing easily precipitating substances that are very hardly processed in the prior art, the background is always calibrated, whereby a measuring apparatus capable of continuously measuring a sample highly accurately and stably for a long time can be provided.

As described above, the present invention can provide a sample treatment apparatus by which a sample containing easily precipitating substances hardly processed in the prior art can be processed continuously and stably for a long time, as well as a measuring apparatus capable of measuring a sample continuously, highly accurately and stably for a long time by using the sample treatment apparatus. Accordingly, the apparatus of the present invention is very useful from the viewpoint of reliability of measurements and rapidness in measurement of sulfur compounds essential for improving the recovery of sulfur in the Claus plant etc.

DETAILED DESCRIPTION OF THE INVENTION

Hereinafter, the embodiment for carrying out the invention is described in detail by reference to the Drawings.

The sample treatment apparatus of the present invention comprises (1) a path for introducing a fluid for an aspirator, (2) at least two sample flow paths A connected in one side to the path for introducing a fluid for an aspirator and connected in the other side to a sample collecting part, (3) a sample flow path B connected in one side to one sample flow path A passing a fluid for an aspirator and connected in the other side to the other sample flow path A, (4) a cooling part for cooling a part of the sample flow paths A, and (5) a controller for selecting and switching the sample flow paths A into which a fluid for an aspirator is introduced.

<Constitutional Example of the Sample Treatment Apparatus of the Present Invention>

Figure 1:
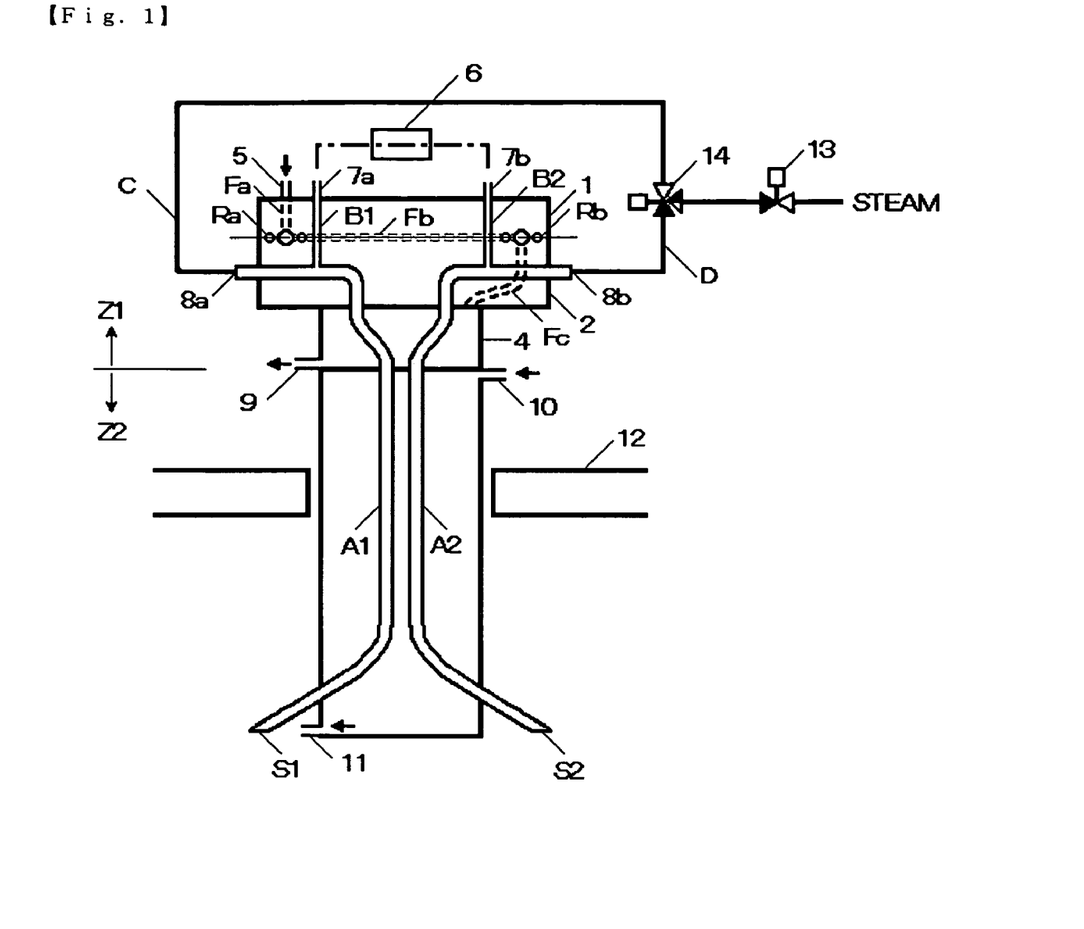
FIG. 1 is an explanatory drawing showing a constitutional example of the sample treatment apparatus of the invention.

The constitutional example of the sample treatment apparatus of the present invention (referred to hereinafter as "the present sample treatment apparatus") is illustrated in FIG. 1. The present sample treatment apparatus is a directly inserted sample treatment apparatus (referred to hereinafter as "the present probe") having a remarkable self-cleaning performance designed to measure a sulfur-rich environment in the sulfur recovery process by the Claus process. The present probe having self-cleaning performance described here can be applied similarly to a similar process where condensing components highly causing interference influence are present. The present probe can achieve the similar function and technical effect to the above not only by directly inserting the probe into the process line, but also by introducing a separately collected sample into the present probe.

Sample gases in the sulfur recovery process by the Claus process are considerably different in composition from one another, depending on the constitution of the process, but generally contain:

| | |
|---|---|
| $H_2S$ | 0 to 2%, |
| $SO_2$ | 0 to 2%, |
| COS | 0 to 5000 ppm, |
| $CS_2$ | 0 to 5000 ppm, | the other substances such as Sv, water, nitrogen oxides (NOx), ammonia ($NH_3$) etc.

As shown in FIG. 1, the present probe having self-cleaning performance is composed of a heating zone Z1 and a cooling zone Z2. The probe shown in the figure has 2 sample treatment systems, but the number and constitution of the sample treatment systems are not limited thereto.

The heating zone Z1 is composed of two flange disks 1, 2 and one hollow cylinder 4. The first disk 1 constitutes a steam inlet 5 for introducing heating steam or heating air (referred to hereinafter as "steam") for heating the heating zone Z1, a flow path Fa for steam in the first disk, and a flow path Fb for heating the first disk 1 and second disk 2. The second disk 2 constitutes a flow path Fb and a flow path Fc for feeding steam to the hollow cylinder 4, simultaneously forms sample flow paths A1 and A2 for two aspirators (having blowback function), and has parts 8a and 8b for introducing a fluid for an aspirator. In the hollow cylinder, steam is introduced through the flow path Fc into the hollow part, and the sample flow paths A1 and A2 are heated by the steam. The steam introduced into the hollow cylinder is discharged from a steam outlet 9. Examples of the fluid for an aspirator can include compressed air and high-temperature (for example 100 to 200° C.) steam. The aspirator function and blowback function will be described later.

The cooling zone Z2 is positioned just below the heating Z1 and constituted such that a part of the sample flow paths A1 and A2 is accommodated in the hollow cylindrical tube, and a refrigerant is introduced from a refrigerant inlet 10 to the hollow part and discharged from a refrigerant outlet 11.

A buffer zone is not required between the heating zone Z1 and cooling zone Z2. This is because occurrence of a rapid change in temperature between the heating zone Z1 and cooling zone Z2 is not problematic for the reason that in the constitution where the sample flow paths A1 and A2 are formed throughout both the heating zone 1 and cooling zone Z2, (1) the heat transfer coefficient of gas is so high that rapid transfer to the determined temperature can be accomplished and (2) in the cooling zone Z2, precipitates are formed at the sides of lower sample collection parts S1 and S2.

Temperature regulation is also used as a means to select a substance removed from the sample. Examples of the refrigerant used can include compressed air, water or a hydrocarbon-based refrigerant.

When the present probe having the structure described above is attached to a process line (not shown in the figure) by flange 12 as shown in FIG. 1, a fluid for an aspirator is connected via an electromagnetic valve 13 and an electromagnetic valve 14 to parts 8a and 8b for introducing a fluid for an aspirator, to control switching of flow paths A1 and A2 functioning as an aspirator or blowback.

In the present probe, a large amount of a fluid for an aspirator is introduced from the parts 8a, 8b for introducing a fluid for an aspirator, into the joining area between the sample flow path B1, B2 as thin tubes (for example, tubes each having an inner diameter of 2 to 6 mm) and the sample flow paths A1, A2 as thick tubes (for example, tubes each having an inner diameter of 8 to 10 mm), whereby the probe functions as an aspirator to suction a sample from the sample flow path A1 or A2 and the sample flow path B1 or B2. Simultaneously, it functions as a blowback, and precipitates in the sample flow paths A1, A2 are removed and simultaneously discharged into the process line. Particularly, in the apparatus like the present probe where the sample is cooled to form precipitates and the precipitates are removed, use of high-temperature steam as the fluid for an aspirator is very effective in removing precipitates adhering to internal walls of the sample flow paths A1 and A2 in a cooled state.

The sample flow path A for introducing a fluid for an aspirator is selected by a controller (not shown in the figure) and switched in a predetermined cycle (for example, several minutes to several hours). Specifically, as illustrated in FIG. 1, high-temperature steam connected to the electromagnetic valve 13 is switched by the electromagnetic valve 14 to the flow path C or D. The flow path C is connected via the part 8c for introducing a fluid for an aspirator to the sample flow path A1, and the flow path D is connected via the part 8b for introducing a fluid for an aspirator to the sample flow path A2, so the sample flow paths A1, A2 can alternately function as an aspirator and function as a remover of precipitates in the sample.

One function as an aspirator is to collect a sample for example by the following procedures:

(1) The electromagnetic valve 13 is opened, and a predetermined amount (for example 10 to 50 L/min. compressed air) of a fluid for an aspirator is introduced into the sample flow path A1 via the electromagnetic valve 14, the flow path C, and the part 8a for introducing a fluid for an aspirator.

(2) In this introduction, the joining area of the sample flow path A1 to the sample flow path B1 forms a depressurized state according to the Bernoulli's law of energy conservation.

(3) By formation of this depressurized state, the sample in the process line is suctioned (for example about 0.1 to 0.5 L/min.) from a sample collecting part S2 via the sample flow path B1, the sample flow path B2 connected thereto, and a flow path connected serially to the sample flow path A2.

(4) The suctioned sample precipitates sulfur etc. onto a wall of the sample flow path A2 in a cooled state, and after the resulting precipitates adhering to the wall are removed, the sample is introduced into the sample flow path B2 in a heated state.

(5) The sample introduced into the sample flow path B2 is mixed via the sample flow path B1 with a fluid for an aspirator and returned via the sample flow path A1 to the process line.

(6) After this state is maintained for a predetermined time (for example, few minutes to several hours), the electromagnetic valve 14 is actuated to switch from the flow path C to the flow path D, and the fluid for an aspirator is introduced into the sample flow path A2.

(7) Similarly to the above-mentioned (2) to (5), a depressurized state in the joining area to the sample flow path B2 is formed, and the sample in the process can be suctioned from the sample collecting part S1.

(8) After this state is maintained for a predetermined time and a stable state is maintained, the electromagnetic valve 14 is actuated to switch the flow path to the state in the above-mentioned (1), and this is periodically repeated.

By alternately switching the two flow paths C and D for introducing a fluid for an aspirator, the function of the aspirator has not only a function in collecting a sample but also a blowback function. The "blowback function" refers generally to a sample treatment function wherein in a flow path through which a sample flows, a large amount of a fluid is introduced in the direction opposite to a sample flow so as to remove the precipitates that are contained in a sample and growing further or adhering to an internal wall of the flow path. That is, in the state (4), sulfur adhering to the wall of the sample flow path A2 in a cooled state gradually grows, and thus it can be estimated:

(1) when this state is continued, the flow path may be narrowed and clogged with precipitates.

(2) as the heat exchange function is deteriorated due to layering of precipitates, the efficiency of removal in the sample flow path A2 is decreased, thus causing an increase in interference influence in a detection system 6 and a subsequent deterioration of measurement accuracy. Accordingly, a fluid for an aspirator can be introduced into the flow path A2 by switching the flow path, thus removing precipitates from the wall and cleaning the sample flow path A2. Particularly by using high-temperature steam, condensation of steam and dissolution of precipitates can be accelerated to further improve the cleaning effect. By returning such precipitates to the process, precipitates can be dissolved to eliminate necessity for separate waste treatment.

In the heating zone Z1, steam is introduced via the steam inlet 5 in the first disk 1 into the present probe to pass through the flow path Fa, and introduced into the flow path Fb between the first disk 1 and the second disk 2. The outlets of the flow paths Fa and Fb are provided with O-ring seals Ra and Rb to prevent leakage. The first disk 1 and the second disk 2 are provided additionally with an O-ring therebetween (not shown in the figure). The steam having passed through the flow path Fb passes through the flow path Fc in the second disk 2, to flow into a hollow cylinder 4 provided therein with a sample flow path A and sample flow path B, and is then discharged from the present probe through a steam outlet 9. The cooling zone Z2 is further positioned just below the heating zone Z1. A buffer zone is not necessary between the heating zone Z1 and the cooling zone Z2.

<First Constitutional Example of the Measuring Apparatus Provided with the Present Sample Treatment Apparatus>

In the measuring apparatus (hereinafter, referred to as "the present measuring apparatus") provided with the present sample treatment apparatus (the present probe), as a constitutional example is shown the present probe arranged by connecting it to a detection system 6 as a separate element shown in the broken line in FIG. 1 through connecting parts 7a and 7b. The measuring apparatus is fundamentally constituted such that the sample flow paths B1 and B2 in the <constitutional example of the present sample treatment apparatus> are connected to the detector system 6 outside the similar function to that of the present probe.

In the detection system 6, detection systems of various measurement principles adapted to measurement components or sample states, including not only a detection system of ultraviolet absorption type described later but also a detection system of infrared absorption type, and a thermal conductivity detection system can be utilized. And also an ion electrode detection system and a specific conductivity detection system can be utilized in a solution.

In the process for recovery of sulfur by the Claus process, examples of the object of measurement include, but are not limited to, $H_2S$ and $SO_2$. For example, $H_2S$, methyl mercaptan ($CH_3SH$), COS or $CS_2$ is the object of measurement in a natural gas treatment process, and $CH_3SH$ or methyl sulfide (($CH_3)_2S$) in addition to $H_2S$ or $SO_2$ is the object of measurement in a paper and pulp manufacturing treatment process.

Accordingly, the sample can be collected and measured in the following procedures. Fundamentally, the measuring apparatus functions in the same manner as in the present probe in the above-described <constitutional example of the present sample treatment apparatus>.

(1) The electromagnetic valve 13 is opened, and a predetermined amount of a fluid for an aspirator is introduced via the electromagnetic valve 14 and the part 8a for introducing a fluid for an aspirator, into the sample flow path A1.
(2) In this introduction, a depressurized state is formed in the joining area between the sample flow path A1 and the sample flow path B1.
(3) By formation of this depressurized state, the sample in the process line is suctioned from a sample collecting part S2 via a flow path connected continuously to a sample flow path B1, a connecting part 7a, a flow path in the detection system 6, a connecting part 7b, a sample flow path B2 and a sample flow path A2.
(4) The suctioned sample precipitates sulfur etc. onto a wall of the sample flow path A2 in a cooled state, and after the resulting precipitates adhering to the wall are removed, the sample is introduced via the sample flow path B2 in a heated state and a connecting part 7b, into a detection system 6 and subjected to measurement. For preventing additional precipitation to prevent interference influence in analysis in the detection system 6, the detection system 6 is also preferably in a heated state.
(5) The measured sample is mixed via a connecting part 7a and sample flow path B1 with a fluid for an aspirator and returned via the sample flow path A1 to the process line.
(6) After stable measurement is carried out while this state is maintained for a predetermined time, the electromagnetic valve 14 is actuated to switch from the flow path C to the flow path D, and the fluid for an aspirator is introduced into the sample flow path A2.
(7) Similarly to the above-mentioned (2) to (5), a depressurized state in the joining area to the sample flow path B2 is formed, and the sample in the process can be suctioned from the sample collecting part S1 and subjected to measurement.
(8) After stable measurement is carried out while this state is maintained for a predetermined time, the electromagnetic valve 14 is actuated to switch the flow path to the state in the above-mentioned (1), and this is periodically repeated.

As described above, the detection system 6 is formed in a flow path for communicating the sample flow paths A1 and A2 with each other, and by the procedures (1) to (8) above, precipitates causing an increase in interference influence etc. in the detection system 6 and subsequent deterioration in measurement accuracy are removed, whereby a measuring apparatus capable of measuring a sample continuously, highly accurately and stably for a long time can be provided.

<Second Constitutional Example of the Measuring Apparatus Provided with the Present Sample Treatment Apparatus>

Figure 2:
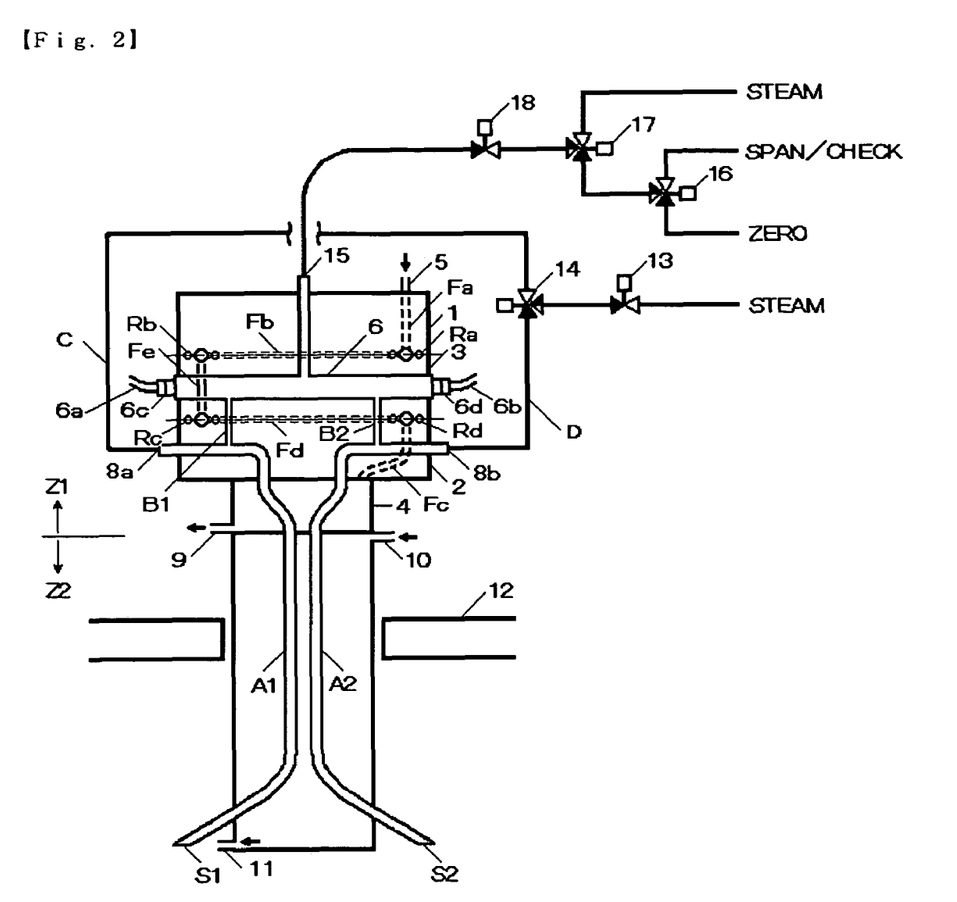
FIG. 2 is an explanatory drawing showing a constitutional example of a measuring apparatus provided with the sample treatment apparatus of the invention.

FIG. 2 shows the second constitutional example of the measuring apparatus provided with the present sample treatment apparatus. The measuring apparatus is constituted such that a third disk 3 accommodating a detection system (specifically a sample cell part) 6 between a first disk 1 and a second disk 2 is added to a cooling zone Z2 in the present sample treatment apparatus. The sample cell part 6 is formed in a flow path for communicating the sample flow paths A1 and A2 with each other, and simultaneously the 3 disks are integrated with one another, whereby the measuring apparatus can be miniaturized, the response is improved. Simultaneously the sample cell part 6 is positioned between the first disk 1 and the second disk 2 to form a heating part, whereby the temperature of the sample cell part 6 is stabilized, generation of precipitates is prevented, and subsequent interference influence can be prevented. In this case, the sample cell part 6 used in the ultraviolet absorption spectrometry is illustrated and described. The details of the analyzer using ultraviolet absorption spectrometry will be described later in detail.

Similar to the sample treatment apparatus, the directly inserted probe having self-cleaning performance in the present measuring apparatus, consists of a heating zone Z1 and a cooling zone Z2, and the heating zone Z1 is composed of three flange disks and one hollow cylinder 4. The second disk 2, the hollow cylinder 4 and the cooling zone Z2 have the same structures and functions as described above. As shown in FIG. 2, the first disk 1 has both a steam inlet 5 for introduction of steam for heating the heating zone 1 and an inlet 15 for introducing a check gas, zero gas, span gas and/or cleaning gas fed to the sample cell part 6. The third disk 3 is provided with the sample cell part 6. Arranging ends 6c and 6d for optical fiber cables 6a and 6b for measuring the process sample by ultraviolet absorption spectrometry are provided in both connecting ends of the sample cell part 6. Steam is supplied into the flow path Fb between the first disk 1 and the third disk 3, and the flow path Fd between the third disk 3 and the second disk 2, and by its heat, the heating zone Z1 can be formed to prevent condensation of the process sample.

The measurement operation of the present measuring apparatus is fundamentally the same as the measurement apparatus according to the first constitutional example, but is different in some aspects arising from integration of the 3 disks with one another, in addition to formation of the sample cell part 6 in a flow path for communicating the sample flow paths A1 and A2 with each other. Hereinafter, the different aspects are mainly described.

(1) The electromagnetic valve 13 is opened, and a predetermined amount of a fluid for an aspirator is introduced via the electromagnetic valve 14 and the part 8a for introducing a fluid for an aspirator, into the sample flow path A1.

(2) In this introduction, a depressurized state is formed in the joining area between the sample flow path A1 and the sample flow path B1.

(3) By formation of this depressurized state, the sample in the process line is suctioned from a sample collecting part S2 via a flow path connected continuously to a sample cell part 6 connected to a sample flow path B1, a sample flow path B2 and a sample flow path A2.

(4) The suctioned sample precipitates sulfur etc. onto a wall of the sample flow path A2 in a cooled state, and after the resulting precipitates adhering to the wall are removed, the sample is introduced via the sample flow path B2 in a heated state into the sample cell part 6 and subjected to measurement. For preventing additional precipitation, the sample cell part 6 is also preferably in a heated state.

(5) The measured sample is mixed via a sample flow path B1 with a fluid for an aspirator and returned via the sample flow path A1 to the process line.

(6) After stable measurement is carried out while this state is maintained for a predetermined time (for example, several minutes to several hours), the electromagnetic valve 14 is actuated to switch the flow path, to introduce the fluid for an aspirator into the sample flow path A2.

(7) In this introduction, similarly to the above-mentioned (2) to (5), a depressurized state in the joining area to the sample flow path B2 is formed, and the sample in the process can be suctioned from the sample collecting part S1 and subjected to measurement.

(8) After stable measurement is carried out while this state is maintained for a predetermined time, the electromagnetic valve 14 is actuated to switch the flow path to the state in the above-mentioned (1), and this is periodically repeated.

As described above, the flow paths in two sample treatment systems are switched mutually, whereby the process sample is collected near to the process line and can be measured rapidly, and at the same time the sample treatment system can be cleaned by blowback.

Figure 3:
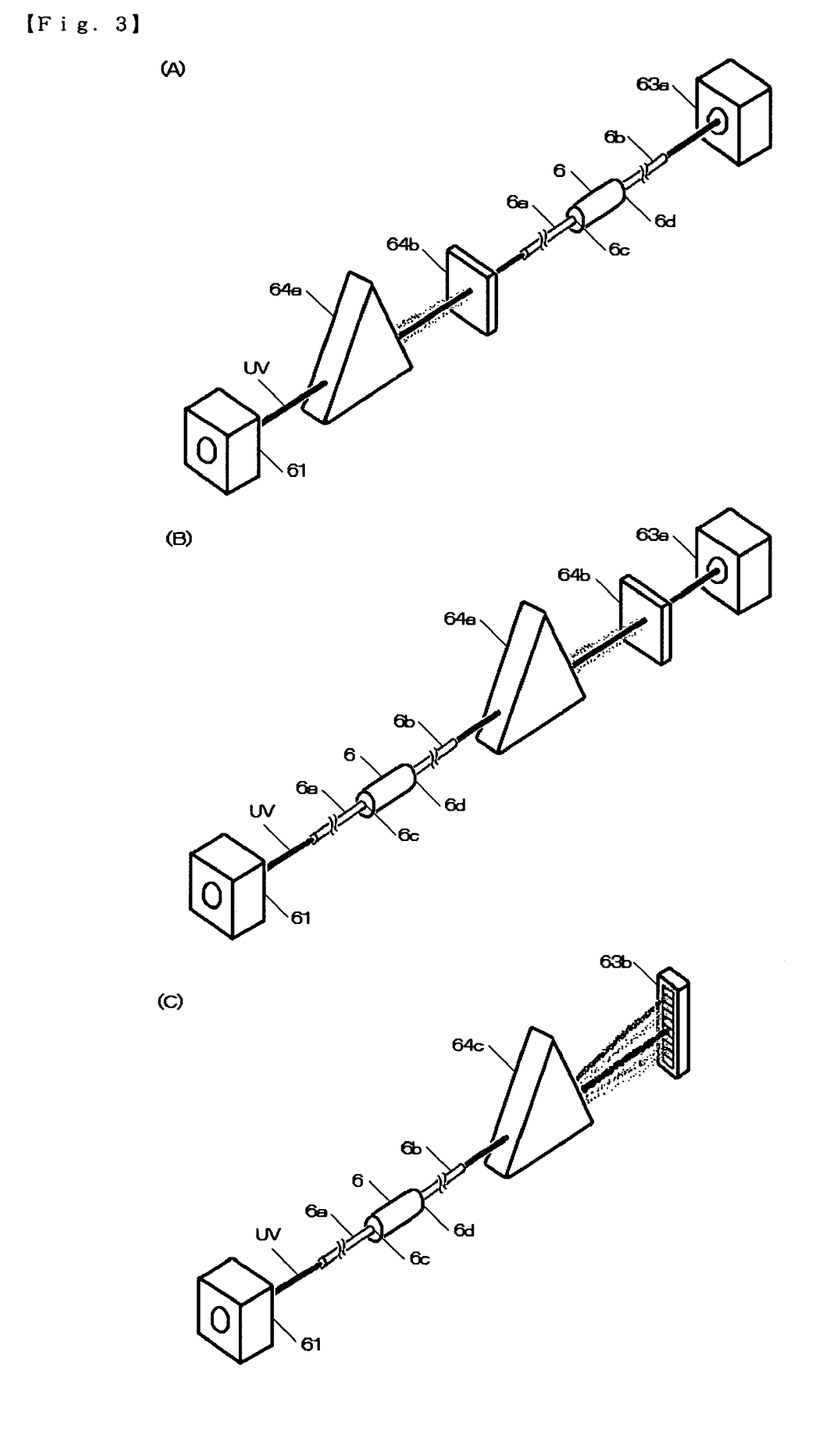
FIG. 3 is an explanatory drawing showing a constitutional example of the ultraviolet absorption type analyzer of the invention.

When the sample cell part 6 is used in the ultraviolet absorption type analyzer, as illustrated generally in FIGS. 3 (A) to (C), an optical system consisting of an ultraviolet light source part 61, a sample cell part 6, an ultraviolet light detector 63a or 63b and spectrometric elements 64a to 64c is formed wherein the amount of the ultraviolet light (corresponding to UV in the figure) absorbed by a measurement component in a sample introduced into the sample cell part 6 is detected with the ultraviolet light detector 63a or 63b, whereby the concentration of the measurement component in the sample can be measured.

Examples of the spectrometric element can include an element wherein a monochromator 64a and slit 64b are combined as shown in FIGS. 3 (A) and (B), whereby the amount of absorbed ultraviolet light in a narrow range is detected by an ultraviolet light detector 63a. The element shown in FIG. 3 (C) uses a polychromator 64c as spectrometric element to enable detection of the amount of absorbed ultraviolet light in a plurality of wavelength ranges by an ultraviolet light detector 63b consisting of a plurality of detection elements.

In the present measuring apparatus, a sample cell part 6, to which both ends 6c and 6d optical fibers 6a and 6b are connected, is accommodated in the third disk 3 and irradiated with an ultraviolet light via the optical fiber 6a from an ultraviolet light source 61. Then a change of the absorbance in the sample cell part 6 is detected via an optical fiber 6b by an ultraviolet light detector 63a or 63b. Since the present probe is near to the process, an optical system liable to the influence of a wide variety of external disturbances such as heat radiation and vibration, particularly the ultraviolet light source 61, the ultraviolet light detector 63a or 64b and the spectrometric elements 64a to 64c can be separated to secure high measurement accuracy.

As the ultraviolet light source 61, a low-pressure mercury lamp, a heavy hydrogen lamp, a xenon lamp etc. are generally used. From the practical viewpoint or in respect of costs, a low-pressure mercury lamp is often used. It also enables to use the so-called "modulation" means wherein the ultraviolet light source 61 is repeatedly turned on/off in a predetermined cycle.

In consideration of workability and strength, the sample cell part 6 can use quartz, glass or a metallic tube of stainless steel or aluminum. As shown in FIG. 3 (A) to (C), the shape is generally in a cylindrical form of about 1 to 500 mm with a cell length determined so as to be adjusted to the concentration of a measurement component, and a substantial length optical path cell utilizing multiple reflection provided therein with a mirror or the like is also utilized frequently. A square pillar cell made of quartz can also be used.

The ultraviolet light is utilized in the range of wavelengths at which other coexistent components show less absorption. For example, wavelengths in the vicinity of 210 to 220 nm are used for measurement of H2S, and wavelengths in the vicinity of 280 to 300 nm are used for $SO_2$. An optical filter called a band pass filter (BPF) allowing lights in the above wavelength range to permeate selectively therethrough is sometimes arranged between the ultraviolet light source part 61 and ultraviolet light detector 63a or 63b, but in the present example, the wavelength is selected depending on a combination of the monochromator 64a and slit 64b as shown in FIG. 3 (A) and FIG. 3 (B), and the amount of light absorbed in the selected wavelength can be detected by the ultraviolet light detector 63a, or as shown in FIG. 3 (C), the light is spectral-diffracted into its spectral component by the polychromator 64c, and the amount of the absorbed light thus spectral-diffracted is monitored in the whole wavelength by an array ultraviolet light detector 63b.

As the ultraviolet light detector 63, a photomultiplier, a silicon photocell or a silicon photodiode can be used, among them the photomultiplier is generally highly sensitive but expensive, and recently a photocell or a photodiode is thus frequently used.

A check gas, zero gas, span gas or cleaning gas is introduced from an inlet 15 into the first disk 1 via an electromagnetic valve 16 for switching between a zero gas (calibration gas) and a span gas (or a check gas), an electromagnetic valve 17 for switching between a calibration gas and a cleaning gas (steam etc.), and an electromagnetic valve 18 for shutting. The introduction and switching of these gases are controlled by the upstream electromagnetic valves 16 to 18. Specifically, the electromagnetic valve 18 can be actuated to introduce a calibration gas into the sample cell part 6 to calibrate the ultraviolet light absorption-type analyzer. When the sample cell part should be cleaned, steam is introduced via the electromagnetic valves 17 and 18 to pass through the first disk 1, and is introduced into the sample cell part 6 in the third disk 3. The steam introduced into the sample cell part 6 dissolves precipitates in the sample cell part 6, and is discharged together with the fluid for an aspirator, from the sample flow path A1 or A2 via the sample flow path B1 or B2 connected to the sample cell part 6.

In the heating zone Z1, steam is introduced via the steam inlet 5 in the first disk 1 into the present probe, to pass through the flow path Fa and then through the flow path Fb between the first disk 1 and the second disk 2. The steam then flows via the flow path Fe arranged in the third disk 3, to pass through the flow path Fd between the third disk 3 and the second disk 2. The inlets and outlets of these flow paths Fb and Fd are provided with O-ring seals Ra and Rb, and Rc and Rd, respectively to prevent leakage. O-rings (not shown in the figure) are additionally arranged between the first disk 1 and the third disk 3 and between the third disk 3 and the second disk 2. The steam passes through the flow path Fd between the third disk 3 and the second disk 2, and then introduced into the second disk 2 and discharged from the third disk 3 via the flow path Fc. The steam is introduced into a hollow cylinder 4 accommodating a part of the flow paths A1 and A2 for an aspirator, heat-exchanged with these flow paths, and discharged from the present probe via the steam outlet 9.

The present measuring apparatus, similar to the sample treatment apparatus, has a cooling zone Z2 cooled with a refrigerant, just below the heating zone Z1. A buffer zone is not necessary between the heating zone Z1 and cooling zone Z2, and condensing components in the process sample are condensed and precipitated in a part of the sample flow paths A1 and A2 accommodated in the cooling zone Z2. Mist not captured in the cooling zone Z2 is gasified in the heating zone Z1 in a latter stage, thus preventing it from exerting interference influence on measurement in the sample cell.

When sample suction is switched to the blowback function, high-temperature steam cleans the material (precipitates) condensed previously in the pipe line. The interval required for this switching is only several minutes to several hours, but in the present measuring apparatus, steam is filled in the sample cell part for only several seconds. During this period, the sample cell part 6 is filled with steam and the analyzer can grasp dark current or background. Simultaneously, this state occurs usually upon switching between an aspirator and blowback, in conjunction with which the dark current or background can be corrected. That is, in the present measuring apparatus, the background in the measurement system can be calibrated by linking with the switching cycle of the fluid for an aspirator. The gas introduced into the sample cell part is not limited to the fluid for an aspirator, and by actuating the electromagnetic valves 17 and 18 with this timing to introduce a cleaning gas, the sample cell part 6, that is, the optical system can be cleaned and simultaneously the background in the measurement system can be calibrated on the basis of the output of the detector. If necessary, a calibration gas is introduced with this timing, whereby the measuring apparatus can be calibrated under conditions where non-measurement time can be as short as possible.

The flow rate of the fluid for an aspirator passing through the sample flow path A1 or A2 is very high, and the flow rate of the sample is low, and thus the cleaning effect in the sample flow path A1 or A2 can be sufficiently secured.

<Constitutional Example of the Present Sample Treatment Apparatus Mounted in the Process Line>

Figure 4:
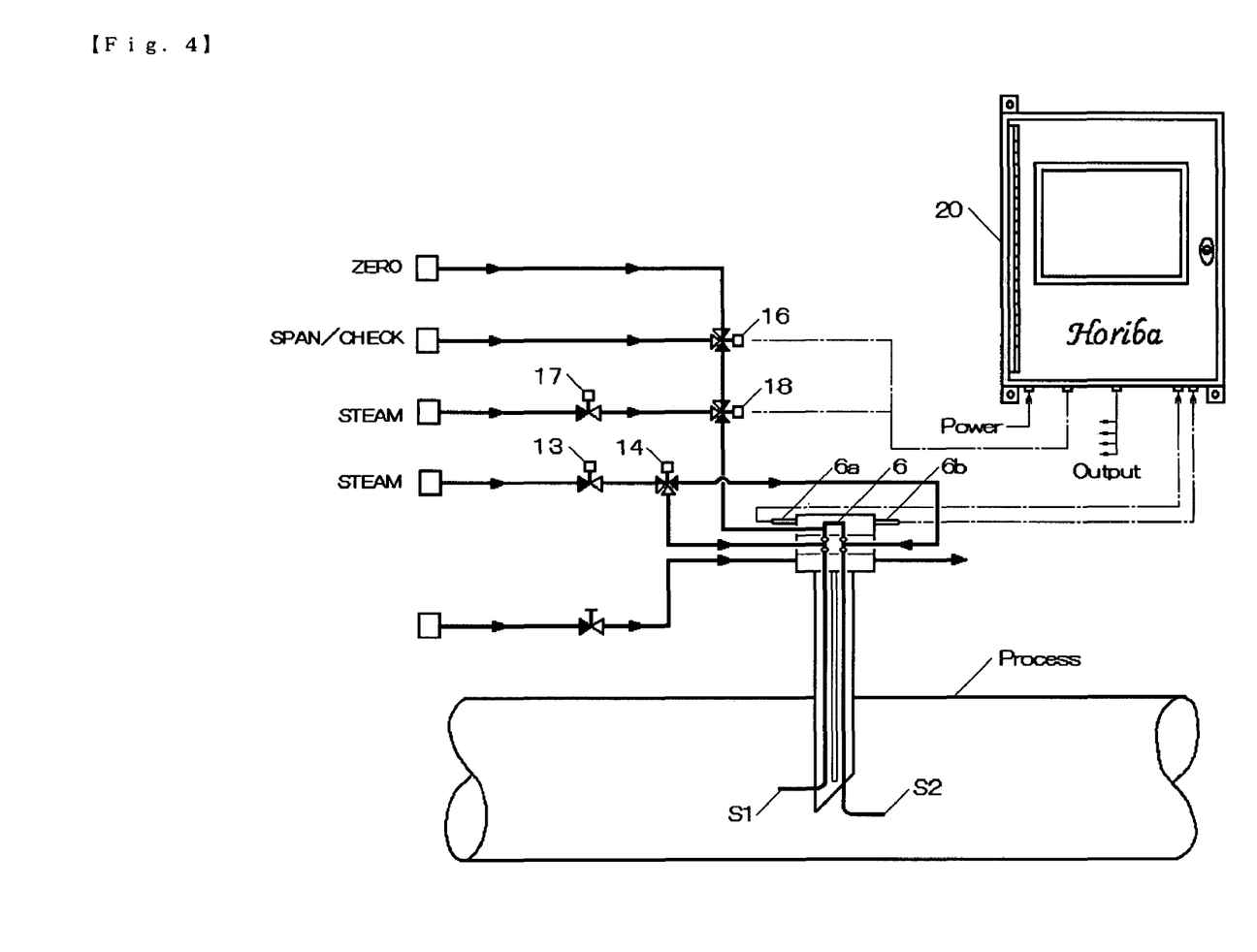
FIG. 4 is an explanatory drawing showing an exterior example of the measuring apparatus of the invention mounted in the process.

Now, the exterior of the measuring apparatus mounted in the process line is shown in FIG. 4. FIG. 4 illustrates the measuring apparatus wherein the present probe having two sample treatment systems suctioning a sample through sample collecting parts S1, S2 alternately and simultaneously discharging a fluid for an aspirator alternately are arranged in the process line, and a gas which was processed to remove condensing substances is introduced into the sample cell part 6 and detected. In addition to the constitution and function of the present measuring apparatus described above, there are arranged a controller 20 for the control of the electromagnetic valves 13 and 14 for switching introduction of steam as a fluid for an aspirator, for the control of the electromagnetic valves 16 to 18 for switching introduction of a calibration gas (including a check gas) and a cleaning gas into the sample cell part 6, and for processing the inputting and outputting of the optical fibers 6a and 6b connected to the sample cell part 6. The controller 20 has not only various kinds of control function of the present probe, but also has functions necessary for maintaining the performance of the measuring apparatus, with respect to the elements in the detection system, for example, the ultraviolet light source and ultraviolet light detector, and the amplifier and converter of output of the ultraviolet light detector, and simultaneously has a function of inputting and outputting signals to the outside or feeding a power source.

As described above, the present invention has been described by reference to application of the sample treatment apparatus and measuring apparatus of probe type having a remarkable self-cleaning performance designed to measure a sulfur-rich environment in the sulfur recovery process mainly by the Claus process, but the present sample treatment apparatus and measuring apparatus can be applied to samples having similar composition, such as process gases containing a specific component, for example, a coal liquefied gas containing a large amount of tar, and to study of various processes.

What is claimed is:

1. A sample treatment apparatus, which comprises:
    a path for introducing a fluid for an aspirator,
    at least two sample flow paths A connected in one side to the path for introducing a fluid for the aspirator and connected in the other side to a sample collecting part,
    a sample flow path B connected in one side to one sample flow path A passing a fluid for the aspirator and connected in the other side to the other sample flow path A,
    a cooling part for cooling a part of the sample flow paths A, and a controller for selecting and switching the sample flow paths A into which a fluid for the aspirator is introduced,
    wherein a fluid for the aspirator is introduced into at least one sample flow path A thereby cleaning one of the sample flow paths A and simultaneously suctioning the sample from at least one sample collecting part connected to the other sample flow path A, cooling the sample in the other sample flow path A, condensing and removing a specific component in the sample, and introducing the sample into the sample flow path B, and simultaneously selecting and switching, in a predetermined cycle, the sample flow path A into which a fluid for the aspirator is introduced.

2. The sample treatment apparatus according to claim 1, wherein the fluid for the aspirator is steam.

3. The sample treatment apparatus according to claim 2, wherein the sample is a process fluid of the Claus process, and at least the sample collecting part is inserted directly into a process line.

4. A measuring apparatus provided with the sample treatment apparatus according to claim 3, wherein the sample flow path B is connected to a sample cell part.

5. A measuring apparatus provided with the sample treatment apparatus according to claim 2, wherein the sample flow path B is connected to a sample cell part.

6. The measuring apparatus according to claim 5, which is provided with a heating part including the sample flow path B and the sample cell part, wherein the heating part can be controlled at temperature higher than in the cooling part.

7. The measuring apparatus according to claim 6, wherein the heating part is divided into a first disk containing a flow path for introducing a heating fluid, a check gas, a calibration gas or a cleaning gas, a second disk for accommodating the sample cell part, and a third disk having a path for introducing a fluid for the aspirator, and is composed of the respective disks connected to one another.

8. The measuring apparatus according to claim 5, wherein an optical fiber is connected to the sample cell part to detect absorbance, thereby measuring the concentration of a specific component in a sample.

9. The measuring apparatus according to claim 5, wherein the background in the measurement system can be calibrated by linking with the switching cycle of the fluid for the aspirator.

10. The sample treatment apparatus according to claim 1, wherein the sample is a process fluid of the Claus process, and at least the sample collecting part is inserted directly into a process line.

11. A measuring apparatus provided with the sample treatment apparatus according to claim 10, wherein the sample flow path B is connected to a sample cell part.

12. The measuring apparatus according to claim 11, which is provided with a heating part including the sample flow path B and the sample cell part, wherein the heating part can be controlled at temperature higher than in the cooling part.

13. The measuring apparatus according to claim 12, wherein the heating part is divided into a first disk containing a flow path for introducing a heating fluid, a check gas, a calibration gas or a cleaning gas, a second disk for accommodating the sample cell part, and a third disk having a path for introducing a fluid for the aspirator, and is composed of the respective disks connected to one another.

14. The measuring apparatus according to claim 11, wherein an optical fiber is connected to the sample cell part to detect absorbance, thereby measuring the concentration of a specific component in a sample.

15. The measuring apparatus according to claim 11, wherein the backgronnd in the measurement system can be calibrated by linking with the switching cycle of the fluid for the aspirator.

16. A measuring apparatus provided with the sample treatment apparatus according to claim 1, wherein the sample flow path B is connected to a sample cell part.

17. The measuring apparatus according to claim 16, which is provided with a heating part including the sample flow path B and the sample cell part, wherein the heating part can be controlled at temperature higher than in the cooling part.

18. The measuring apparatus according to claim 17, wherein the heating part is divided into a first disk containing a flow path for introducing a heating fluid, a check gas, a calibration gas or a cleaning gas, a second disk for accommodating the sample cell part, and a third disk having a path for introducing a fluid for the aspirator, and is composed of the respective disks connected to one another.

19. The measuring apparatus according to claim 16, wherein an optical fiber is connected to the sample cell part to detect absorbance, thereby measuring the concentration of a specific component in a sample.

20. The measuring apparatus according to claim 16, wherein the background in the measurement system can be calibrated by linking with the switching cycle of the fluid for the aspirator.

* * * * *